US012121338B2

(12) United States Patent
Smits et al.

(10) Patent No.: US 12,121,338 B2
(45) Date of Patent: Oct. 22, 2024

(54) HEART MONITORING SYSTEM AND METHOD

(71) Applicant: Nederlandse Organisatie voor toegepast-natuurwetenschappelijk onderzoek TNO, 's-Gravenhage (NL)

(72) Inventors: Edsger Constant Pieter Smits, Eindhoven (NL); Daniele Raiteri, Eindhoven (NL); Jeroen Van Den Brand, Goirle (NL)

(73) Assignee: Nederlandse Organisatie voor toegepast-natuurwetenschappelijk onderzoek TNO, 's-Gravenhage (NL)

( * ) Notice: Subject to any disclaimer, the term of this patent is extended or adjusted under 35 U.S.C. 154(b) by 349 days.

(21) Appl. No.: 17/624,006

(22) PCT Filed: Jul. 22, 2020

(86) PCT No.: PCT/NL2020/050480
§ 371 (c)(1),
(2) Date: Dec. 30, 2021

(87) PCT Pub. No.: WO2021/015617
PCT Pub. Date: Jan. 28, 2021

(65) Prior Publication Data
US 2022/0346656 A1 Nov. 3, 2022

(30) Foreign Application Priority Data
Jul. 23, 2019 (EP) .................................... 19187908

(51) Int. Cl.
*A61B 5/02* (2006.01)
*A61B 5/00* (2006.01)
(Continued)

(52) U.S. Cl.
CPC ........ *A61B 5/0255* (2013.01); *A61B 5/02444* (2013.01); *A61B 5/6891* (2013.01); *A61B 5/721* (2013.01); *A61B 5/7267* (2013.01)

(58) Field of Classification Search
CPC ........ A61B 2090/064; A61B 2090/065; A61B 2018/00875; A61B 2562/0219;
(Continued)

(56) References Cited

U.S. PATENT DOCUMENTS

| 2014/0039351 A1 | 2/2014 | Mix et al. |
| 2016/0213309 A1 | 7/2016 | Sannholm et al. |
| 2017/0258336 A1* | 9/2017 | Furness, III ........... A61B 5/026 |

FOREIGN PATENT DOCUMENTS

| CN | 206792383 U | 12/2017 |
| JP | 10014889 A | 1/1998 |
| JP | 2015188698 A | 11/2015 |

OTHER PUBLICATIONS

European Patent Office, International Search Report in corresponding International Application No. PCT/NL2020/050480, dated Nov. 9, 2020 (2 pages).

(Continued)

*Primary Examiner* — Deborah L Malamud
(74) *Attorney, Agent, or Firm* — Leydig, Voit & Mayer, Ltd.

(57) ABSTRACT

A heart monitoring system (100) comprises an array of force-sensitive resistors (10) spanning a sensor surface (50). Each resistor (10) is configured to change a respective resistance value (R) in accordance with an amount of static pressure (P) exerted on the sensor surface (50) at a respective location of the force-sensitive resistor (10) by a subject (200). An array of piezoelectric transducers (20) is interspersed among the array of force-sensitive resistors (10). Each transducer (20) is configured to generate 10 a respective time-dependent electrical signal (S) in accordance with (Continued)

respective vibrations (F) exerted on the sensor surface (50) at a respective location of the transducer (20) by the subject (200). A controller (30) is configured to determine a heart rate (H1) of the subject (200) based on a combination of the measured resistance values (R) of the force-sensitive 15 resistors (10) and the time-dependent electrical signals (S) of the piezoelectric transducers (20).

20 Claims, 3 Drawing Sheets

(51) Int. Cl.
*A61B 5/024* (2006.01)
*A61B 5/0255* (2006.01)

(58) Field of Classification Search
CPC ........ A61B 5/0205; A61B 2017/00026; A61B 2562/0247; A61B 5/486; A61B 17/320068; A61B 5/00; A61B 5/02427; A61B 5/024; A61B 2034/2048; A61B 2017/00044; A61B 2017/0011; A61B 2017/00402; A61B 5/7264; A61B 2562/06; A61B 5/1107; A61B 2018/0088; A61B 2562/04; A61B 2562/043; A61B 5/02; A61B 5/68; A61B 5/6801; A61B 5/6885; A61N 1/36185; A61N 1/36125; A61N 1/36135; A61N 1/3702; A61N 1/36014
See application file for complete search history.

(56) References Cited

OTHER PUBLICATIONS

Japanese Patent Office, Notice of Reasons for Rejection in corresponding Japanese Patent Application No. 2022-500494 mailed Apr. 16, 2024.

* cited by examiner

HEART MONITORING SYSTEM AND METHOD

CROSS-REFERENCE TO RELATED APPLICATIONS

This patent application is a U.S. National Phase of PCT International Application No. PCT/NL2020/050480, filed Jul. 22, 2020, which claims priority to European Application No. 19187908.9, filed Jul. 23, 2019, which are both expressly incorporated by reference in their entireties, including any references contained therein.

TECHNICAL FIELD AND BACKGROUND

The present disclosure relates to systems and methods for measuring heart rate.

For example, piezoelectric sensors can be used for performing ballistocardiography (BCG) to measure the heart rate, breathing rate and even pulse wave velocity in a semi-contact manner through clothing or bedding/matrass (e.g. chair/bed). Preferably, the sensors need to be in proximity to relevant parts of the body to transfer the vibrations. Unfortunately this contact information is difficult to extract from the sensor signal. As a consequence artefacts are quite common and this is worse when the position of the subject is undefined.

U.S. 2018/0337325A1 describes a multi-element piezo sensor for in-bed physiological measurements. The monitoring system can perform a first scan of all of the piezo sensors. The first scan can be, for example, a high-level scan to determine roughly where the user is located along the mat. The monitoring system can perform a second scan of one or more piezo sensors, such as piezo sensors potentially located in the immediate periphery of the user's body. The piezo sensors that are potentially located in the immediate periphery of the user's body can be, for example, those piezo sensors measuring a force, while also located adjacent to piezo sensors that do not measure force.

However, piezoelectric sensors typically produce time-dependent signals which may need individual and continuous monitoring. It can also be difficult to balance the accuracy for different time scales and pressure ranges. There remains a need for further improvements in accuracy heart rate monitoring.

SUMMARY

Aspects of the present disclosure relate to a heart monitoring system and method. As described herein, the heart monitoring system preferably uses a sensor surface with a combination of (membrane based) force-sensitive resistors and piezoelectric transducers. The force sensitive resistors can be configured to measure a respective amount of pressure exerted on the sensor surface by a subject. For example, the force sensitive resistors may change a respective resistance value dependent on the pressure. The piezoelectric transducers can be interspersed among, e.g. between, the force-sensitive resistors and configured to measure respective vibrations exerted on the sensor surface at a respective location of the transducer by the subject. For example, the piezoelectric transducers can produce time-dependent electrical signals dependent on the vibrations. The heart rate of the subject can be determined based on a combination of the respective signals from the different types of sensors, e.g. the measured resistance values of the force-sensitive resistors and the time-dependent electrical signals of the piezoelectric transducers.

Using the force-sensitive resistors, the (static) pressure profile of a subject can be more accurately determined, than using piezo-electric sensors. For example, the force sensitive resistors can be arranged in a (relatively) high density grid, e.g. with shared scan lines in a passive matrix configuration. As will be appreciated, the force sensitive resistors may be better suited to measure a range of different pressure signals and in a high density grid can be used to accurately determine a pressure profile. Using the accurate pressure profile information of the force sensitive resistors, a better selection can be made which of the piezoelectric transducers will likely produce the best signals. For example, the pressure profile can be used to determine regions of the body where the heart rate vibrations are most prominent. For example, the piezoelectric transducers can be arranged in a (relatively) low density grid, e.g. to allow dedicated circuit lines between the relatively few transducers and the controller. In this way rapidly changing signals such as heart beat can be unambiguously and accurately measured from specific locations. This can improve reliability and data integrity. The data from the pressure sensor may also be used for a number of other applications such as breathing, posture detection, et cetera. This can further enhance the applications of the sensors.

BRIEF DESCRIPTION OF DRAWINGS

These and other features, aspects, and advantages of the apparatus, systems and methods of the present disclosure will become better understood from the following description, appended claims, and accompanying drawing wherein:

DESCRIPTION OF EMBODIMENTS

Figure 1A:
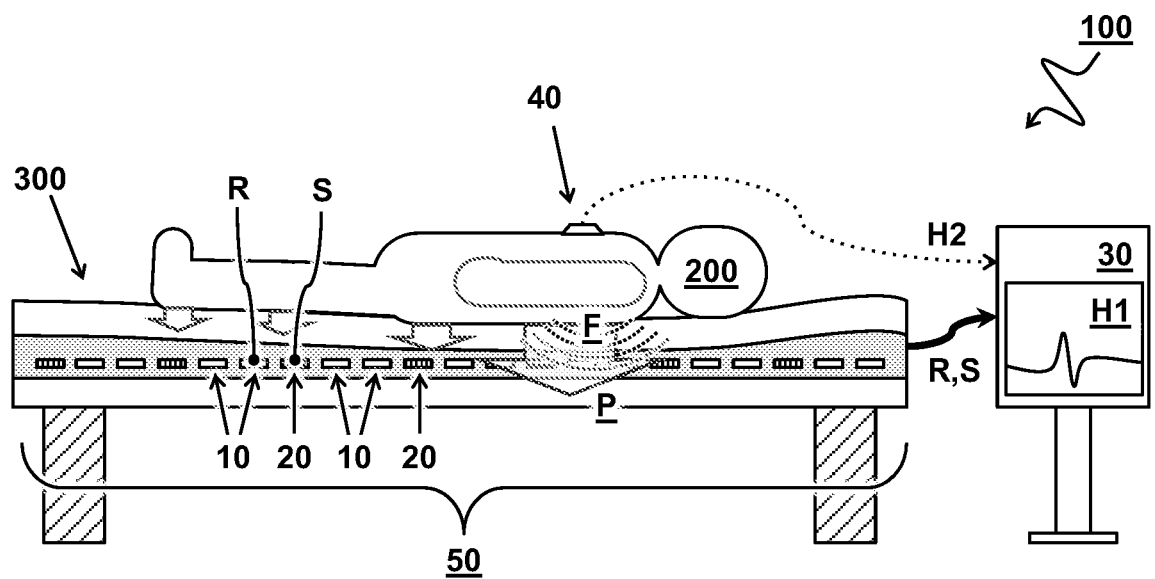
FIG. 1A illustrates an exemplary embodiment of a heart monitoring system.

Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise it will be understood that when a connection between structures or components is described, this connection may be established directly or through intermediate structures or components unless specified otherwise.

Aspects of the present disclosure relate to performing data fusion to improve the reliability of piezo sensors for the detection of heart beat or other physiological parameters such as respiration rate. Preferably, a combination of piezo sensors and membrane based pressure sensors is used. For example, based on the pressure sensor distribution, the piezoelectric sensors with the highest likelihood of good signal integrity can be selected.

In some embodiments, quasi-static pressure distributions onto an object, e.g. bed, seat, baby bed, garment, is first detected using pressure sensor technology, e.g. based on Thermoplastic Polyurethane (TPU) technology. Using the pressure distribution, piezo sensors with the highest likeliness of providing the accurate data can be used to extract a heart rate and/or breathing rate measurement. Preferably, the piezo sensors are printed.

In some embodiments, the pressure sensors are used to reconstruct how someone is laying onto the sensors. This can help the piezo sensor readout, e.g. because the pressure sensors can provide a low power solution to detect if there is a person or an object present on the sensor system. Accordingly, the obtained pressures distribution can be used to reconstruct a model of the person on the pressure sensor. In one embodiment, the piezo sensors are exclusively readout when a human body is detected. This may save computationally heavy analysis in other circumstances when it is not needed. In another or further embodiment, based on a combination of physical location with respect to the body and body parts, e.g. arm, leg, neck, the sensors located on the best body parts for detecting the BCG are extracted and within this group of piezo sensors, the piezo sensors within the optimal pressure range are selected.

In some embodiments, piezo sensors having a high likeliness not to be in contact with the body are used for noise cancellations, e.g. to remove unrelated (e.g. parasitic) vibrations. In other or further embodiments, sensors which are located on parts of the body where no BCG signal should be present are used to remove other vibrations, e.g. related to breathing and not heart rate, or vice versa (in case the breathing rate is measured). In some embodiments, the breathing rate of a subject is extracted simultaneously from the pressure sensor signal and the piezo sensors providing a redundancy on the obtained signal. Advantageously, motion artefacts can be actively suppressed since motions of a subject are detected using the pressure sensor. Alternatively, or in addition, the motion artefacts can be removed spatially and/or temporally.

Using a piezo resistive sensor array, data which is directly relevant to improving signal quality can be provided by defining the most accurate place to measure and measuring real-time spatial and temporal low frequency motions, e.g. below 1 Hz. It will be appreciated that using an absolute pressure distribution provides much more relevant data for improving the measurements, compared to for example using only piezo sensors. Advantageously, the static pressure sensor information can be used to better filter the piezo date and to complement (in the case of breathing rate) the piezo sensor data.

In some embodiments, stretchable inks and TPU technology are used for the manufacturing of the sensors. Accordingly, the sensors may be located closer to the persons body, which improves the reliability of the signals. In other or further embodiments, the measurements may be complemented by incorporating (printed) temperature sensors in the sensor surface to, for example, measure a temperature in a bed or chair.

The invention is described more fully hereinafter with reference to the accompanying drawings, in which embodiments of the invention are shown. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

FIG. 1A illustrates an exemplary embodiment of a heart monitoring system 100.

In some embodiments, e.g. as shown, the heart monitoring system 100 comprises an array of force-sensitive resistors 10 spanning a sensor surface 50, e.g. substrate. In one embodiment, each resistor 10 is configured to change a respective resistance value "R" in accordance with an amount of (quasi) static pressure "P" exerted on the sensor surface 50 at a respective location of the force-sensitive resistor 10 by a subject 200. In other or further embodiments, the system comprises an array of piezoelectric transducers 20 interspersed among the array of force-sensitive resistors 10, e.g. on the same or another (overlapping) substrate. In one embodiment, each transducer 20 is configured to generate a respective time-dependent electrical signal S in accordance with respective vibrations "F" exerted on the sensor surface 50 at a respective location of the transducer 20 by the subject 200. In a preferred embodiment, e.g. as shown, a controller 30 is configured to determine a heart rate "H1" of the subject 200 based on a combination of the measured resistance values "R" of the force-sensitive resistors 10 and the time-dependent electrical signals "S" of the piezoelectric transducers 20.

The heart monitoring system 100 as described herein may find application in various settings and situations. In one embodiment, e.g. as shown, aspects or applications, can be embodied as a bed 300 comprising the heart monitoring system 100 as described herein. In some embodiments, a mattress of a bed 300 comprises a heart monitoring system 100 for a subject 200 to lie on. In some embodiments, e.g. as shown, the sensor surface 50 is embedded in the mattress. Alternatively, the sensor surface 50 may be disposed on top of the mattress. In other or further embodiments, the sensor surface 50 may be disposed between one or more sheets or other bedding. For example, the subject 200 may be a patient who needs continuous monitoring lying in a hospital bed. The heart monitoring system can also be incorporated in other types of furniture, e.g. a chair (not shown). For example, the system can be incorporated in the bottom and/or back section of the chair, e.g. regular chair or car seat. For example, the sensor surface 50 including the force-sensitive resistors 10 and piezoelectric transducers 20 may be clamped onto the seat back and disposed on top of the seat bottom. Alternatively, or additionally, the sensor surface 50 may be embedded in an internal layer of the seat, e.g. inside a seat cushion.

In a preferred embodiment, e.g. as shown, the controller 30 receives the measured resistance values "R" of the force-sensitive resistors 10 and the time-dependent electrical signals "S" of the piezoelectric transducers 20 as an input, and produces a heart rate "H1" as an output. Accordingly, the heart monitoring system 100 may provide a continuous, real-time measurement and analysis of the subject's 200 heart rate, even when the subject (200) is in non-direct contact with the sensor surface 50. In some embodiments, e.g. as shown, the controller 30 may be provided as an external device to the bed 300. For example, the controller 30 is connected with an electrical connection to the bed 300. Alternatively, the controller 30 may be provided as part of the bed 300. In one embodiment, e.g. as shown, a display device is connected to the controller 30. The heart rate can also be output in other ways, e.g. as a an electrical data signal for further processing, or an audible or haptic signal.

In some embodiments, as shown in FIG. 1A, a secondary heart monitoring device 40 may be temporarily or permanently provided and coupled to the controller 30. In some embodiments, the secondary heart monitoring device 40 is attached to the subject's 200, e.g. wrist or chest, for a period of time to produce a secondary heart rate measurement H2 which can be used as a reference value. For example, the secondary heart controller 30 can compare the secondary heart rate measurement H2 to the primary measurement of the heart rate "H1". In the embodiment shown, the secondary heart rate measurement H2 is measured using a separate instrument, e.g. a dedicated secondary heart monitoring device 40 based on electrical signals from the heart region (electrocardiogram). In some embodiments, the secondary heart monitoring device 40 may be provided temporarily, as check and/or to correct the primary heart monitoring system 100. Alternatively, the secondary heart monitoring device, e.g. electrodes on the chest, can be removed once the network has been trained, as will be explained later in FIGS. 3A and 3B.

In some embodiments, e.g. as shown, the subject's weight, position or movement may cause a static or quasi-static pressure "P" onto the sensor surface 50. For example, the pressure "P" may be relatively high in specific areas, e.g. higher at the subject's chest area compared to the subject's legs. In a preferred embodiment, the pressure profile is used to determine where the heart rate is measured. Static pressure can be distinguished from dynamic vibrations "F" such as heart rate, e.g. based on time scale. As will be appreciated, a force sensitive resistor, is typically capable of measuring static pressures, i.e. even if the pressure is constant in time. Of course, the pressure may change, e.g. by the subject moving, which will result in a new (static) pressure being measured. This may be contrasted with the measurements using piezo-electric sensors, which are typically more sensitive to vibrations or pressure changes.

Figure 1B:
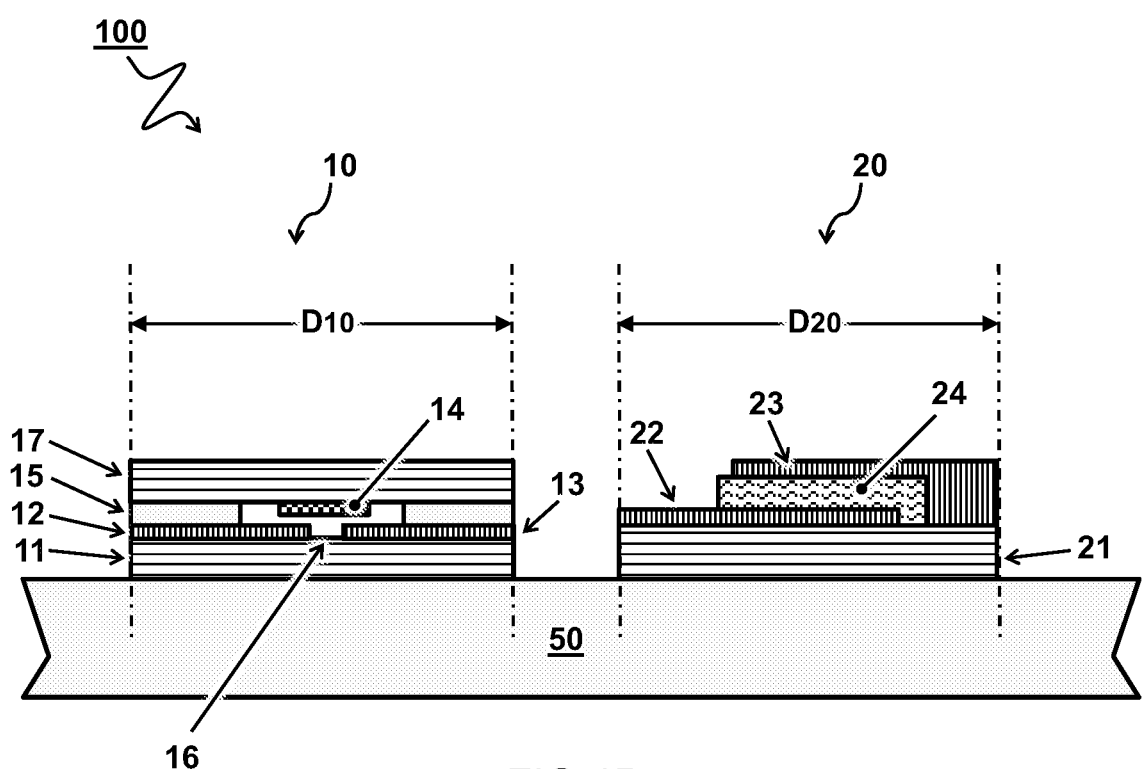
FIG. 1B illustrates a cross-section view of a heart monitoring system with a force-sensitive resistor and a piezo-electric transducer.

FIG. 1B illustrates a cross-section view of a heart monitoring system 100 with a force-sensitive resistor 10 and a piezoelectric transducer 20.

In a preferred embodiment, the force-sensitive resistors 10 are arranged on or spanning the sensor surface 50. Most preferably, the force-sensitive resistors 10 are distributed with equally spacing over the sensor surface 50. This may allow easy correspondence between respective signals and location of the sensors. In another or further embodiment, the force-sensitive resistors 10 may vary in distribution, orientation, number and/or shape. This may allow, e.g. a higher concentration of sensors at relevant locations.

Typically, each of the force-sensitive resistors 10 comprises a force-sensitive material 14, e.g. a conductive composite material or other material which changes its resistance when a force is applied in a membrane configuration. In one embodiment, e.g. as shown, the force-sensitive material 14 disposed on a first flexible substrate 17, e.g. a thermoplastic polyurethane (TPU) substrate, wherein the force-sensitive material 14 is facing a set of electrodes 12,13 disposed on an opposing second substrate 11, e.g. a TPU substrate. In another or further embodiment, e.g. as shown, the force-sensitive material 14 is held apart from the electrodes 12,13 by a spacer material 15 disposed between the substrates 17,11 and surrounding the force-sensitive material 14. In some embodiments, e.g. as shown, the first 17 and/or second substrate 11 is configured to flex towards the opposing substrate under the influence of static pressure "P" applied to the force-sensitive resistors 10. Accordingly, the force-sensitive material 14 contacts the electrodes 12,13 and changes the resistance value "R". In another or further embodiment, when there is no pressure applied, the sensor acts like an infinite resistor, i.e. an open circuit. Preferably, the more pressure is applied to the surface of the sensor, the more the electrodes 12,13 touch the force-sensitive material 14, and the lower the resistance becomes. Preferably, the force-sensitive resistors have a diameter D10 on the order of a few millimeters. For example, between one millimeter and fifty millimeters, preferably between five millimeters and twenty millimeters, for example ten millimeters.

In a preferred embodiment, piezoelectric transducers 20 are interspersed among the force-sensitive resistors 10. Typically, each of the piezoelectric transducers 20 comprises a layer of piezoelectric material 24. Preferably, the piezoelectric material 24 is made of a polymer, e.g. PVDF-TrFE, which has a piezoelectric effect. The piezoelectric effect can be understood as a phenomenon whereby electric charges and corresponding fields may accumulate in certain materials in response to applied mechanical stress. For example, a piezoelectric transducer 20 may detect small changes in pressure, acceleration, temperature, strain, or force and convert them into an electrical signal.

In one embodiment, e.g. as shown, the piezoelectric material 24 is sandwiched between a bottom electrode 22 and top electrode 23. In some embodiments, the bottom electrode 22 is disposed on a substrate 21, e.g. a TPU substrate. Preferably, the piezoelectric transducers 20 are configured to generate a respective time-dependent electrical signal S in response to a time dependent mechanical stress being applied to the piezoelectric material 24. Preferably, the piezoelectric transducers have a diameter D20 on the order of a few millimeters. For example, between one millimeter and fifty millimeters, preferably between five millimeters and twenty millimeters, for example ten millimeters.

Figure 2:
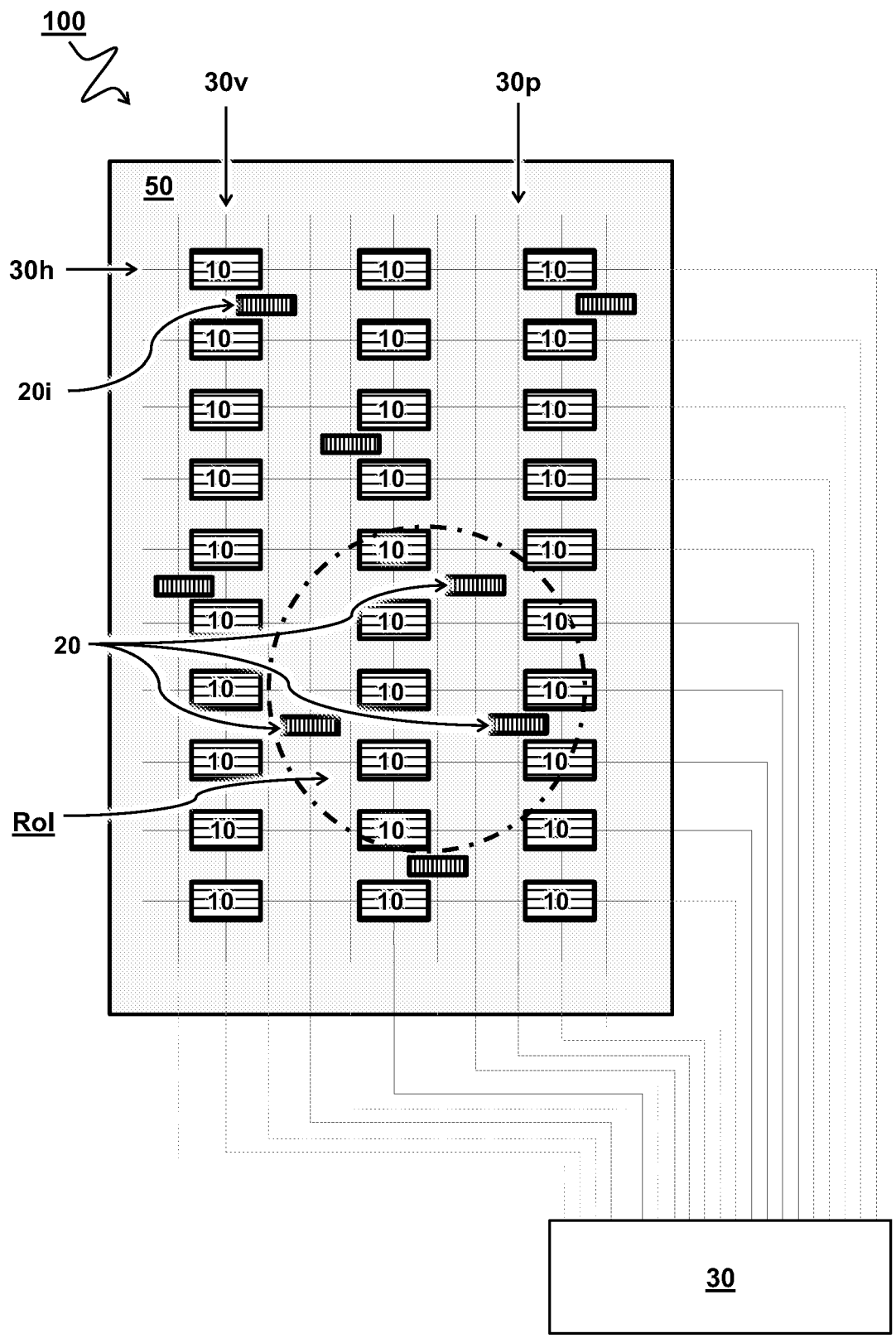
FIG. 2 illustrates a schematic layout of sensors on a sensor surface in a heart monitoring system and their connection with a controller.

FIG. 2 illustrates a schematic layout of sensors 10,20 on a sensor surface 50 in a heart monitoring system 100 and respective connections with a controller 30.

As described herein, the sensor surface 50 can be formed by one or more substrates housing the sensors. For example, the force-sensitive resistors 10 and/or piezoelectric transducers 20 can be distributed (interspersed) on a single substrate, or each type sensor may be disposed on a respective substrate. While the present figure shows the force-sensitive resistors 10 and piezoelectric transducers 20 disposed on top of a substrate 50, in other embodiments the substrates 11,21 of the sensors may be part of the sensor surface.

In one embodiment, e.g. as shown, each of the force-sensitive resistors 10 is coupled to a pair of shared circuit lines $30h,30v$. For example, each shared circuit line connects a plurality of the force-sensitive resistors 10 to the controller 30. Accordingly a resistance value "R" of a respective force-sensitive resistors 10 can be determined e.g. by scanning a respective pair of the shared circuit lines $30h,30v$ connected to said force-sensitive resistors 10. For example, as shown in FIG. 2, the first row of force-sensitive resistors 10 are horizontally coupled to a shared circuit line 30h, and the first column of force-sensitive resistors 10 are also coupled to a shared circuit line 30v. In another or further embodiment, e.g. the multiple shared circuit lines 30v,30h are coupled to the controller 30 from one side, and to a ground on the other side. Of course also other configurations are possible.

In another or further embodiment, e.g. as shown, each of the piezoelectric transducers 20 is separately coupled with a dedicated circuit line 30p to the controller 30. Piezoelectric transducers 20 may typically use a dedicated circuit line 30p, e.g. because they produce single time-dependent electrical signals which is preferably detected individually. For example, the first piezoelectric transducer 20 on the first column of the array is individually coupled with a dedicated circuit line 30p to the controller 30 from one side and to a ground from the other side. In other embodiments, any other suitable means for coupling the force-sensitive resistors 10 and piezoelectric transducers 20 to the controller 30 is contemplated.

In a preferred embodiment, the sensor surface 50 comprises more force-sensitive resistors 10 than piezoelectric transducers 20. For example, the force-sensitive resistors are arranged in a relatively high density grid while the piezoelectric transducers are arranged in a relatively low density grid. For example, the number of force-sensitive resistors 10 can be higher than the number of piezoelectric transducers 20 by at least a factor of two, three, four or five. It will be appreciated that it may be easier to connect many force-sensitive resistors 10 than piezoelectric transducers 20, e.g. owing to the differing signals and/or connections. This can be used to advantage in providing a better measurement of the pressure profile using the force-sensitive resistors 10 while using the few interspersed piezoelectric transducers 20 to measure heart rate at specific locations, e.g. based on the profile.

In one embodiment, the multiple shared circuit lines 30v,30h and dedicated circuit lines 30p form a matrix readout system. In another or further embodiment, the controller 30 is configured to determine a pressure profile based on the measured resistance values (R) of the force-sensitive resistors 10. In some embodiments, the pressure profile is used to determine a region of interest (RoI) based on locations of corresponding force-sensitive resistors 10 on the surface 50. For example, the region of interest is the region of the sensor surface 50 that the subject 200 is contacting. In a preferred embodiment, the controller 30 is configured to analyze a shape and/or magnitude of the pressure profile to overlay a shape of the subject's body. In another or further preferred embodiment, the region of interest is determined at one or more specific locations in the pressure profile corresponding to respective location on the subject's body.

In one embodiment, the controller 30 is configured to exclusively or predominantly select the piezoelectric transducers 20 located in the region of interest, for measuring the respective time-dependent electrical signals "S". Accordingly, the heart rate "H1" is determined by measuring vibrations "F" using a subset of the piezoelectric transducers 20 located on the surface 50 in the region of interest. For example, the region of interest is the region of the sensor surface 50 wherein the BCG signal of the subject 200 is optimal. In some embodiments, only the piezoelectric transducers 20 located in the region of interest are active. It will be appreciated that this way, the controller does not have to continuously monitor all the piezoelectric transducers 20 on the sensor surface 50.

In some embodiments, at least one of the piezoelectric transducers 20 outside a region of interest based on the force-sensitive resistors 10, is used for noise cancellation. For example, after determining the region of interest, one or more piezoelectric transducers 20i outside the region of interest may be used to cancel noise by cancelling any vibrations "F" detected by the inactive piezoelectric transducers 20i. It will be appreciated that this way vibrations "F" that are not induced by the contact of the subject 200 with the sensor surface 50, and any background noise will be cancelled and not taken into consideration while measuring the heart rate "H1".

Figure 3A:
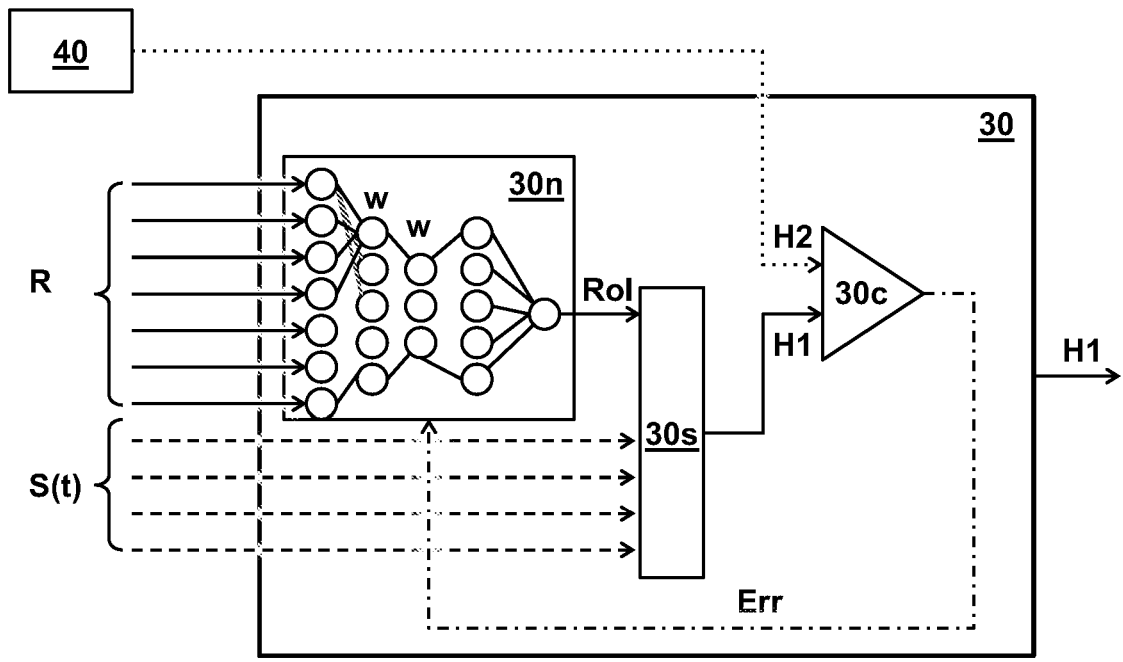
FIGS. 3A and 3B illustrate examples of machine learning to improve determination of a heart rate using a neural network.
Figure 3B:
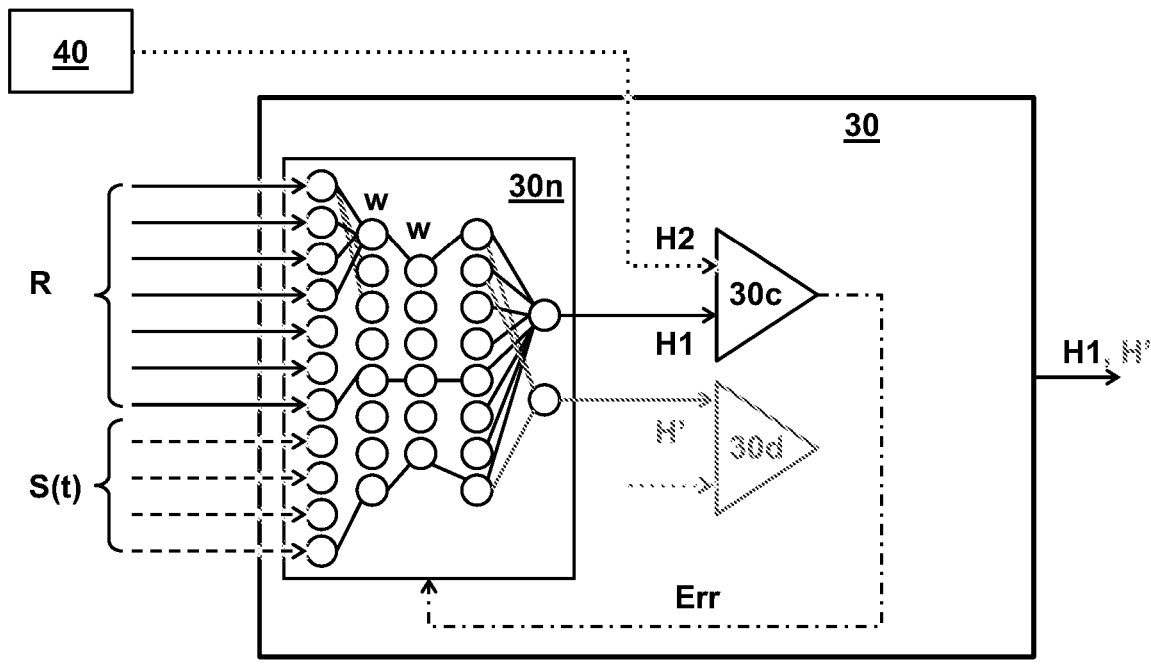

FIGS. 3A and 3B illustrate examples of machine learning to improve determination of a heart rate "H1" using a neural network 30n.

In one embodiment, e.g. as shown in FIG. 3A, the controller 30 comprises a neural network 30n configured to receive at least the resistance values "R" to determine a region of interest. For example, the resistance values "R" are fed as input into the neural network 30n and the neural network is trained to output a region of interest. In a preferred embodiment, e.g. as shown, based on the region of interest determined by the neural network, a selection is made from one or more of the time-dependent electrical signals "S(t)" for determining a primary measurement of the heart rate "H1". In some embodiments, the network is trained for each individual subject to provide optimal accuracy taking into account specific characteristics of the subject. In other or further embodiments, the network is generally trained to be used also for other subjects. Also combinations are possible, e.g. the network starts with a basic training which can be improved for a specific individual. For example, the trained network may comprise a set of weights (w), offsets or other parameters which determine the network to output a region of interest and/or heart rate based on the respective input signals.

In another or further embodiment, e.g. as shown in FIG. 3B, the time-dependent electrical signals "S(t)" can be input into the same or another neural network for determining a respective heart rate measurement. For example the resistance values "R" and time-dependent electrical signals "S" are fed as input into a neural network 30n. In a preferred embodiment, the neural network 30n is configured to output a value indicative of a primary measurement of the heart rate "H1".

In some embodiments, e.g. as shown in both FIGS. 3A and 3B, the primary measurement of the heart rate "H1" is compared to a secondary measurement of heart rate "H2", obtained by an independent heart monitoring device 40, for training the neural network 30n. For example, the neural network 30n may be trained by comparing a direct or indirect output from the neural network 30n with the secondary heart rates of the secondary heart monitoring device 40. For example, the difference between the primary and secondary heart rate measurements is fed back as an error "Err" into the network, which may result in changes to the weights "w" or other parameters of the neuron connections.

In some embodiments, a recurrent neural network (RNN) is used. This is a class of artificial neural networks where connections between nodes form a directed graph along a temporal sequence. This allows it to exhibit temporal dynamic behavior, e.g. a time dependent heart rate signal. Also other or similar artificial networks can be used. Also other or further values H' can be output from the neural network 30n, or the controller 30 in general. For example, the neural network 30n may output physiological parameters such a breathing rate, blood pressure, weight, posture detection, body position, body temperature, et cetera.

For the purpose of clarity and a concise description, features are described herein as part of the same or separate embodiments, however, it will be appreciated that the scope of the invention may include embodiments having combinations of all or some of the features described. Some aspects of the present disclosure relate to a non-transitory computer-readable medium storing instructions. In some embodiments, the non-transitory computer-readable when executed by a controller in a heart monitoring system causes the system to determine the heart rate of a subject directly or indirectly contacting the sensor surface. Other aspects of the present disclosure relate to a method for heart monitoring. In some embodiments, the method comprises providing an array of force-sensitive resistors spanning a sensor surface. In one embodiment, each resistor is configured to change a respective resistance value in accordance with an amount of quasi static pressure exerted on the sensor surface at a respective location of the force-sensitive resistor by a subject. In other or further embodiments, the method comprises providing an array of piezoelectric transducers interspersed among the array of force-sensitive resistors. In one embodiment, each transducer is configured to generate a respective time-dependent electrical signal in accordance with respective vibrations exerted on the sensor surface at a respective location of the transducer by the subject. In a preferred embodiment, the method comprises determining a heart rate of the subject based on a combination of the measured resistance values of the force-sensitive resistors and the time-dependent electrical signals of the piezoelectric transducers.

In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. Where one claim refers to another claim, this may indicate synergetic advantage achieved by the combination of their respective features. But the mere fact that certain measures are recited in mutually different claims does not indicate that a combination of these measures cannot also be used to advantage. The present embodiments may thus include all working combinations of the claims wherein each claim can in principle refer to any preceding claim unless clearly excluded by context.

The invention claimed is:

1. A heart monitoring system comprising:
an array of force-sensitive resistors spanning a sensor surface, wherein each force-sensitive resistor, of the array of force-sensitive resistors, is configured to change a respective resistance value in accordance with an amount of static pressure exerted, by a subject, on the sensor surface at a respective location of the force-sensitive resistor;
an array of piezoelectric transducers, wherein ones of the piezoelectric transducers are interspersed between ones of the force-sensitive resistors, wherein each transducer of the array of piezoelectric transducers is configured to generate a respective time-dependent electrical signal in accordance with respective vibrations exerted, by the subject, on the sensor surface at a respective location of the transducer; wherein the sensor surface has a quantity of force-sensitive resistors that exceeds a quantity of piezoelectric transducers; and
a controller configured with executable instructions that, when executed, facilitate the controller determining a heart rate of the subject based on a combination of:
the measured resistance values of ones of the array of force-sensitive resistors, and
the time-dependent electrical signals of ones of the array of piezoelectric transducers,
wherein, in accordance with the determining a heart rate of the subject, the controller is configured to;
measure, using measurements of the force-sensitive resistors, a pressure profile of the static pressure exerted, by the subject, on the sensor surface;
determine, based on the pressure profile, one or more specific locations of the sensor surface;
select a piezoelectric transducer subset, of the ones of the array of piezoelectric transducers interspersed between ones of the force-sensitive resistors, corresponding to the one or more specific locations of the sensor surface; and
measure the heart rate of the subject using the piezoelectric transducer subset.

2. The system according to claim 1, wherein the controller is configured to determine the pressure profile based on the measured resistance values of the ones of the array of force-sensitive resistors, wherein the pressure profile is used to determine a region of interest based on locations of corresponding force-sensitive resistors on the surface, wherein the heart rate is determined by measuring vibrations using a subset of the piezoelectric transducers located on the surface in the region of interest.

3. The system according to claim 2, wherein the controller is configured to analyze a parameter of the pressure profile to overlay a shape of the subject's body,
wherein the parameter is at least one parameter type taken from the group consisting of:
a shape of the pressure profile, and
a magnitude of the pressure profile; and
wherein the region of interest is determined at one or more specific locations in the pressure profiled corresponding to a respective location on the subject.

4. The system according to claim 2, wherein at least one piezoelectric transducer, of the array of piezoelectric transducers, outside the region of interest based on the force-sensitive resistors, is used for noise cancellation.

5. The system according to claim 1, wherein the resistance values are fed as input into a neural network, wherein the neural network is trained to output a region of interest, and
wherein, based on the region of interest, a selection is made from one or more of the time-dependent electrical signals for determining a primary measurement of the heart rate.

6. The system according to claim 1, wherein the resistance values and time-dependent electrical signals are fed as input into a neural network, and
wherein the neural network is configured to output a value indicative of a primary measurement of the heart rate.

7. The system according to claim 5, wherein the primary measurement of the heart rate is compared to a secondary measurement of heart rate, obtained by an independent heart monitoring device, for training the neural network.

8. The system according to claim 1, wherein each force-sensitive resistor, of the array of force-sensitive resistors, comprises a force-sensitive material disposed on a first substrate facing a set of electrodes disposed on an opposing, second substrate,
- wherein the force-sensitive material is held apart from the electrodes by a spacer material that is disposed between the substrates and surrounds adjacent sides of the force-sensitive material, and
- wherein the first substrate and/or the second substrate is configured to flex towards the opposing substrate under the influence of static pressure applied to the force-sensitive resistors, thereby contacting the force-sensitive material with the electrodes and changing the resistance value.

9. The system according to claim 1, wherein each piezoelectric transducer, of the array of piezoelectric transducers, comprises a layer of piezoelectric material sandwiched between a bottom electrode and a top electrode, and
- wherein each piezoelectric transducer is configured to generate a respective time-dependent electrical signal in response to a time dependent mechanical stress applied to the layer of piezoelectric material of the respective piezoelectric transducer.

10. The system according to claim 1, wherein each force-sensitive resistor, of the array of force-sensitive resistors, is coupled to a pair of shared circuit lines,
- wherein each shared circuit line connects a plurality of force-sensitive resistors, of the array of force-sensitive resistors to the controller,
- wherein a resistance value of a respective force-sensitive resistor of the array of force-sensitive resistors is determined by scanning a respective pair of the shared circuit lines connected to respective force-sensitive resistors of the array of force-sensitive resistors.

11. The system according to claim 1, wherein each piezoelectric transducer, of the array of piezoelectric transducers, is separately coupled with a respective dedicated circuit line to the controller.

12. The system according to claim 1, wherein the sensor surface contains a quantity of the force-sensitive resistors that is at least twice a quantity of piezoelectric transducers.

13. The heart monitoring system according to claim 1, wherein the heart monitoring system is configured to form a part of a bed or chair.

14. A non-transitory computer-readable medium storing instructions that, when executed by a controller in a heart monitoring system, causes the heart monitoring system to determine a heart rate of a subject directly or indirectly contacting a sensor surface of the heart monitoring system,
- wherein the heart monitoring system comprises:
  - an array of force-sensitive resistors spanning a sensor surface, wherein each force-sensitive resistor, of the array of force-sensitive resistors, is configured to change a respective resistance value in accordance with an amount of static pressure exerted, by a subject, on the sensor surface at a respective location of the force-sensitive resistor; and
  - an array of piezoelectric transducers, wherein ones of the piezoelectric transducers are interspersed between ones of the force-sensitive resistors, wherein each transducer of the array of piezoelectric transducers is configured to generate a respective time-dependent electrical signal in accordance with respective vibrations exerted, by the subject, on the sensor surface at a respective location of the transducer; wherein the sensor surface has a quantity of force-sensitive resistors that exceeds a quantity of piezoelectric transducers;
- wherein the heart rate of the subject is determined, by the controller executing the instructions, based on a combination of:
  - the measured resistance values of ones of the array of force-sensitive resistors, and
  - the time-dependent electrical signals of ones of the array of piezoelectric transducers, and
- wherein the instructions, when executed by the controller, facilitate the controller cooperatively operating with the array of force-sensitive resistors and the array of piezoelectric transducers to carry out a method wherein the heart rate of the subject is determined, the method comprising:
  - measuring, using measurements of the force-sensitive resistors, a pressure profile of the static pressure exerted, by the subject, on the sensor surface;
  - determining, based on the pressure profile, one or more specific locations of the sensor surface;
  - selecting a piezoelectric transducer subset, of the ones of the array of piezoelectric transducers interspersed between ones of the force-sensitive resistors, corresponding to the one or more specific locations of the sensor surface; and
  - measuring the heart rate of the subject using the piezoelectric transducer subset.

15. A method for heart monitoring, the method comprising:
- providing an array of force-sensitive resistors spanning a sensor surface, wherein each force-sensitive resistor, of the array of force-sensitive resistors, is configured to change a respective resistance value in accordance with an amount of static pressure exerted, by a subject, on the sensor surface at a respective location of the force-sensitive resistor;
- providing an array of piezoelectric transducers, wherein ones of the piezoelectric transducers are interspersed between ones of the force-sensitive resistors, wherein each transducer, of the array of piezoelectric transducers is configured to generate a respective time-dependent electrical signal in accordance with respective vibrations exerted, by the subject, on the sensor surface at a respective location of the transducer, wherein the sensor surface has a quantity of force-sensitive resistors that exceeds a quantity of piezoelectric transducers; and
- determining a heart rate of the subject based on a combination of:
  - the measured resistance values of ones of the array of force-sensitive resistors, and
  - the time-dependent electrical signals of ones of the array of piezoelectric transducers;
- wherein, during the determining a heart rate of the subject, a controller cooperatively operates with the array of force-sensitive resistors and the array of piezoelectric transducers to perform the following:
  - measuring, using measurements of the force-sensitive resistors, a pressure profile of the static pressure exerted, by the subject, on the sensor surface;
  - determining, based on the pressure profile, one or more specific locations of the sensor surface;
  - selecting a piezoelectric transducer subset, of the ones of the array of piezoelectric transducers interspersed between ones of the force-sensitive resistors, corresponding to the one or more specific locations of the sensor surface; and
  - measuring the heart rate of the subject using the piezoelectric transducer subset.

16. The method according to claim 15, wherein the pressure profile is determined based on the measured resistance values of the ones of the array of force-sensitive resistors, wherein the pressure profile is used to determine a region of interest based on locations of corresponding force-sensitive resistors on the surface, wherein the heart rate is determined by measuring vibrations using a subset of the piezoelectric transducers located on the surface in the region of interest.

17. The method according to claim 16, wherein a shape and/or magnitude of the pressure profile is analyzed to overlay a shape of the subject's body,
wherein the region of interest is determined at one or more specific locations in the pressure profiled corresponding to a respective location on the subject.

18. The method according to claim 16, wherein at least one piezoelectric transducer, of the array of piezoelectric transducers outside the region of interest based on the force-sensitive resistors, is used for noise cancellation.

19. The method according to claim 15, wherein the resistance values are fed as input into a neural network,
wherein the neural network is trained to output a region of interest,
wherein, based on the region of interest, a selection is made from one or more of the time-dependent electrical signals for determining a primary measurement of the heart rate.

20. The method according to claim 15, wherein the resistance values and time-dependent electrical signals are fed as input into a neural network,
wherein the neural network is configured to output a value indicative of a primary measurement of the heart rate, and
wherein the primary measurement of the heart rate is compared to a secondary measurement of heart rate, obtained by an independent heart monitoring device, for training the neural network.

* * * * *